(12) United States Patent
Stumbo et al.

(10) Patent No.: US 6,310,687 B1
(45) Date of Patent: Oct. 30, 2001

(54) LIGHT DETECTION DEVICE WITH MEANS FOR TRACKING SAMPLE SITES

(75) Inventors: David P. Stumbo, Belmont; Douglas N. Modlin, Palo Alto, both of CA (US)

(73) Assignee: LJL Biosystems, Inc., Sunnyvale, CA (US)

( * ) Notice: Subject to any disclaimer, the term of this patent is extended or adjusted under 35 U.S.C. 154(b) by 0 days.

(21) Appl. No.: 09/768,765

(22) Filed: Jan. 23, 2001

Related U.S. Application Data

(63) Continuation of application No. PCT/US00/18547, filed on Jul. 7, 2000.
(60) Provisional application No. 60/142,721, filed on Jul. 7, 1999.

(51) Int. Cl.[7] .................................................. G01N 21/64
(52) U.S. Cl. ...................... 356/317; 356/417; 250/458.1; 422/63; 422/82.08
(58) Field of Search ...................... 356/317, 318, 356/417; 250/458.1, 459.1, 461.1, 461.2; 422/63, 65, 82.05, 82.08

(56) References Cited

U.S. PATENT DOCUMENTS 5,645,800 * 7/1997 Masterson et al. ................ 422/65
5,888,454 * 3/1999 Leistner et al. .................... 422/65

* cited by examiner

Primary Examiner—F. L. Evans
(74) Attorney, Agent, or Firm—Kolisch Hartwell Dickinson McCormack & Heuser

(57) ABSTRACT

Apparatus and methods for optical detection with improved read speed and/or signal-to-noise ratio. These apparatus and methods may involve among others moving an sample substrate (108) while simulataneously detecting light transmitted from one or more sample sites (110) on the substrate (108) by sequentially tracking the sample sites (110) as they move. A stage (101), movable in a first direction, supports the substrate (108). A detector (118) detects light emanating from an examination region (102) delimited by a detection initiation position (106a) and a detection termination position (106b). An optical relay structure (122) transmit light from the examination region (102) to the detector (118). A scanning mechanism (120) simultaneously moves the optical relay structure (122) and the substrate in the first direction. The optical relay structure (122) tracks the substrate (108) between the detection initiation position (106a) and the detection termination position (106b).

34 Claims, 10 Drawing Sheets

SECOND ELLIPSE IS OPTIONAL, CAN ALSO WORK WITH 1 NON-DICHROIC

LIGHT DETECTION DEVICE WITH MEANS FOR TRACKING SAMPLE SITES

CROSS-REFERENCE

This application is a continuation of PCT Patent Application Ser. No. PCT/US00/18547, filed Jul. 7, 2000, which is incorporated herein by reference.

This application is based upon and claims priority from U.S. Provisional Patent Application Ser. No. 60/142,721, filed Jul. 7, 1999, which is hereby incorporated by reference.

This application incorporates by reference the following U.S. patent application Ser. No. 08/840,553, filed Apr. 14, 1997; Ser. No. 08/929,095, filed Sep. 15, 1997, now abandoned; Ser. No. 09/118,141, filed Jul. 16, 1998; Ser. No. 09/144,575, filed Aug. 31, 1998, now U.S. Pat. No. 6,159,425; Ser. No. 09/144,578, filed Aug. 31, 1998; Ser. No. 09/146,081, filed Sep. 2, 1998, now U.S. Pat. No. 6,187,267; Ser. No. 09/156,318, filed Sep. 18, 1998; Ser. No. 09/160,533, filed Sep. 24, 1998, now U.S. Pat. No. 6,097,025; Ser. No. 09/302,158, filed Apr. 29, 1999; Ser. No. 09/349,733, filed Jul. 8, 1999; Ser. No. 09/468,440, filed Dec. 21, 1999; Ser. No. 09/478,819, filed Jan. 5, 2000; Ser. No. 09/494,407, filed Jan. 28, 2000; Ser. No. 09/556,030, filed Apr. 20, 2000; and Ser. No. 09/596,444, filed Jun. 19, 2000.

This application also incorporates by reference the following PCT patent application Ser. No. PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; Ser. No. PCT/US99/16453, filed Jul. 21, 1999; Ser. No. PCT/US99/16621, filed Jul. 23, 1999; Ser. No. PCT/US99/16286, filed Jul. 26, 1999; Ser. No. PCT/US99/16287, filed Jul. 26, 1999; Ser. No. PCT/US99/24707, filed Oct. 19, 1999; Ser. No. PCT/US00/00895, filed Jan. 14, 2000; Ser. No. PCT/US00/03589, filed Feb. 11, 2000; Ser. No. PCT/US00/04543, filed Feb. 22, 2000; Ser. No. PCT/US00/06841, filed Mar. 15, 2000; Ser. No. PCT/US00/12277, filed May 3, 2000; Ser. No. PCT/US00/15774, filed Jun. 9, 2000; Ser. No. PCT/US00/16012, filed Jun. 9, 2000; and Ser. No. PCT/US00/16025, filed Jun. 9, 2000.

This application also incorporates by reference the following U.S. provisional patent application Ser. No. 60/143,185, filed Jul. 9, 1999; Ser. No. 60/153,251, filed Sep. 10, 1999; Ser. No. 60/164,633, filed Nov. 10, 1999; Ser. No. 60/165,813, filed Nov. 16, 1999; Ser. No. 60/167,301, filed Nov. 24, 1999; Ser. No. 60/167,463, filed Nov. 24, 1999; Ser. No. 60/178,026, filed Jan. 26, 2000; Ser. No. 60/182,036, filed Feb. 11, 2000; Ser. No. 60/182,419, filed Feb. 14, 2000; Ser. No. 60/184,719, filed Feb. 24, 2000; Ser. No. 60/184,924, filed Feb. 25, 2000; Ser. No. 60/190,265, filed Mar. 17, 2000; Ser. No. 60/191,890, filed Mar. 23, 2000; Ser. No. 60/193,586, filed Mar. 30, 2000; Ser. No. 60/197,324, filed Apr. 14, 2000; Ser. No. 60/200,530, filed Apr. 27, 2000; Ser. No. 60/200,594, filed Apr. 28, 2000; and Ser. No. 60/202,087, filed May 4, 2000.

This application also incorporates by reference the following publications: K. E. van Holde, *Physical Biochemistry* ($2^{nd}$ ed. 1985); William Bains, *Biotechnology from A to Z* (1993); Richard P. Haugland, *Handbook of Fluorescent Probes and Research Chemicals* ($6^{th}$ ed. 1996); Joseph R. Lakowicz, *Principles of Fluorescence Spectroscopy* ($2^{nd}$ ed. 1999); Bob Sinclair, *Everything's Great When It Sits on a Chip: A Bright Future for DNA Arrays,* 13 The Scientist, May 24, 1999, at 18; and Charles R. Cantor and Paul R. Schimmel, *Biophysical Chemistry* (1980).

FIELD OF THE INVENTION

The invention relates to optical detection. More particularly, the invention relates to apparatus and methods for optical detection with improved read speed and/or signal-to-noise ratio. The apparatus and methods may be used with microplates, biochips, chromatography plates, microscope slides, and other substrates for high-throughput screening, genomics, SNPs analysis, pharmaceutical research and development, life sciences research, and other applications.

BACKGROUND OF THE INVENTION

Optical spectroscopy is the study of the interaction of light with matter. Typically, optical spectroscopy involves monitoring some property of light that is changed by its interaction with matter, and then using that change to characterize the components and properties of a molecular system. Recently, optical spectroscopy has been used in high-throughput screening procedures to identify candidate drug compounds.

Optical spectroscopy is a broad term that describes a number of methods, such as absorption, luminescence (such as photoluminescence and chemiluminescence), scattering/reflectance, circular dichroism, optical rotation, and optical microscopy/imaging, among others. In turn, each of these terms describes a number of more closely related methods; for example photoluminescence includes fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Unfortunately, optical detection systems for use in optical spectroscopy suffer from a number of shortcomings. In particular, optical detection systems generally involve alignment of a sample and portions of an optical relay structure (such as an optics head) for directing light to and from the sample. Such alignment may be accomplished by physically moving the sample relative to the optical relay structure, or by physically moving the optical relay structure relative to the sample. Typically, such movement is followed by a waiting period before measurement to permit vibrations to subside. Time spent during alignment and subsequent waiting periods is downtime because it is time during which data cannot be collected from the sample. Such downtime is especially significant in high-throughput screening, where tens or hundreds of thousands of samples must be aligned with an optical relay structure to conduct a particular study.

In principle, the number of alignment steps can be reduced by reading simultaneously from a plurality of samples or from a larger area of a single sample. However, simultaneous reading typically will reduce intensities, because excitation light is distributed to a larger area and because the distance between the sample and optical relay structure is increased. Reduced intensities may decrease signal-to-noise ratios, decreasing reliability, especially with less intense nonlaser light sources.

SUMMARY OF THE INVENTION

The invention provides apparatus and methods for optical detection with improved read speed and/or signal-to-noise ratio.

DETAILED DESCRIPTION OF THE INVENTION

The invention provides apparatus and methods for optical detection with improved read speed and/or signal-to-noise ratio. These apparatus and methods may involve among others moving a sample substrate while simultaneously detecting light transmitted from one or more sample sites on the substrate by sequentially tracking the sample sites as they move. In this way, downtime associated with starting and stopping the sample substrate and with an inability to read during or immediately after moving the substrate may be reduced or eliminated. The following examples illustrate without limitation additional aspects of the invention.

EXAMPLE 1

Figure 1:
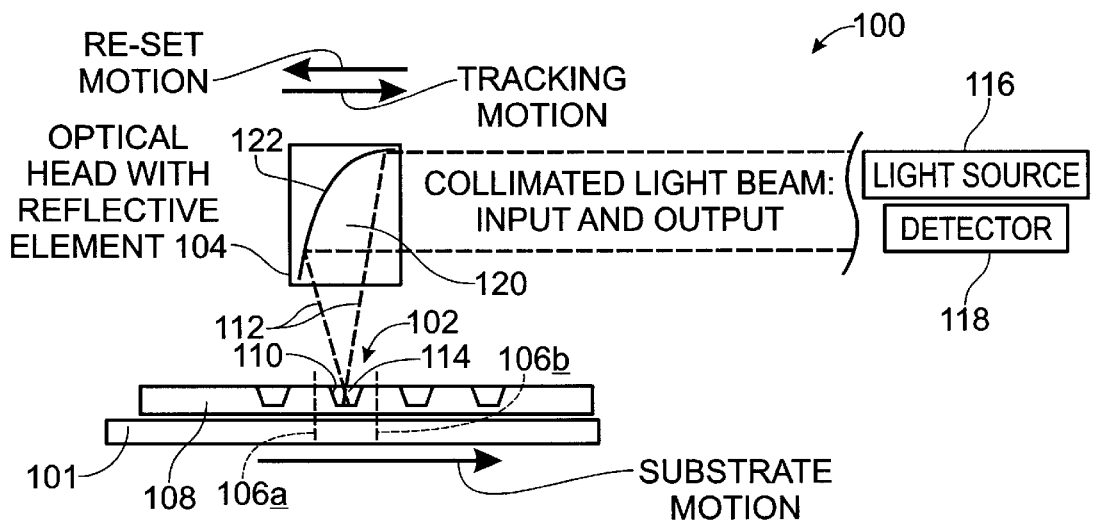
FIG. 1 is a schematic view of a light detection device constructed in accordance with aspects of the invention, showing the device in use to read from a substrate.

FIG. 1 shows a light detection device 100 constricted in accordance with aspects of the invention. Device 100 includes a stage 101, an examination region 102, and an optics head 104. Examination region 102 is delimited by a detection initiation position 106a and a detection termination position 106b. Stage 101 may be used to support a substrate 108 having a plurality of sample sites 110, such as a microplate and associated microplate wells, and optics head 104 may be used to direct light 112 to and/or from a sensed volume 114 positioned in a sample site located in the examination region. Specifically, light may be directed to the sample site from a light source 116, and/or light may be directed from the substrate to a detector 118. Typically, the examination region will be larger than the sensed volume, and the separation between adjacent/examined sample sites will be larger than the separation between the initiation position and the termination position. Suitable substrates, light sources, detectors, and optical relay structures for directing light to an optics head and substrate from a light source, and from a substrate and optics head to a detector are described below.

Device 100 also includes a scanning mechanism 120 configured to scan the substrate, so that device 100 may read from a plurality of positions on the substrate. In device 100, scanning mechanism 120 includes a reflective surface 122 and is configured simultaneously to move (at least a portion of) the optics head and substrate, preferably in a single direction. The optics head tracks the substrate between detection initiation position 106a and detection termination position 106b, and signal is collected continuously during an integration time over which there typically is no substantial relative motion between the optics head and the sample being analyzed. After the integration time, the position of the sensed volume (or optical beam) may be reset to the detection initiation position so that the sensed volume can track and detect from the next sample site on the substrate. If the reset time is small compared to the integration time, the percentage of time lost will be small. The scanning mechanism improves read time by reducing the time that the detection optics spends over areas of the substrate that do not contain sample to be interrogated. (Any time spent over such areas can be considered downtime.) The scanning mechanism also improves read time because the substrate moves continuously, more rapidly bringing new areas of the substrate into position for reading, and because the need for a waiting period for vibrations to subside is reduced or eliminated if the substrate does not jostle the samples by starting, stopping, or otherwise significantly changing speed. In this regard, the sample sites may move at a substantially constant speed, at least through the examination region.

Device 100 may use any of various strategies to read from multiple sample sites. The device can read from the sample sites sequentially, one-by-one, as described above, or it can read from the sites in groups of two or more. Here, such reading groups may be parallel or perpendicular to the direction of reading, or a combination thereof. The device also can read from a first array in a first direction, move or offset in a second (typically perpendicular) direction, and then read again in the first direction from a second array parallel to the first array. Mechanisms for moving a sample substrate in one, two, or three directions are described in PCT Patent Application Ser. No. PCT/US00/12277, filed May 3, 2000, which is incorporated herein by reference.

Signal from samples on the (moving) substrate may be read by point-to-point reading or by constant velocity scanning. In point-to-point reading, the optics head is fixed relative to the substrate, as described above, while the signal from the detector is integrated for a desired period. In constant velocity scanning, the optical beam is moved relative to the substrate, while the signal from the detector is "binned" into pixels. The size of each pixel is simply the product of the scanning speed (relative to the substrate speed) and the integration time. For example, if the (relative) scanning speed is 10 mm per second and the integration time is 100 milliseconds, the pixel size is 1 mm.

With this technique, a point-to-point reading detection system can read photoluminescent samples essentially as rapidly as a charge-coupled device (CCD)-based reading system with an equivalent light source and numerical aperture. This is because the light source is the limitation, not the detector. A CCD is faster for chemiluminescence, because it collects the light emitted (which is not affected by detector area) from all samples simultaneously. The light output of each well is decreased in large-area photoluminescence, because the illumination per well is reduced, so that the increased speed resulting from collecting light from all wells in parallel is cancelled by the reduced illumination per well. nevertheless, the invention can be effective with fluorescence, phosphorescence, and chemiluminescence measurements, because for a given total read time, more time is spent integrating signal, and less time is spent aligning the optics with new samples. The invention is particularly effective with fluorescence polarization measurements, because good signal-to-noise ratios preferably involve collection of a minimum number of photons (e.g., 10,000) during the integration period, as described in U.S. patent application Ser. No. 09/349,733, which is incorporated herein by reference.

Figure 2:
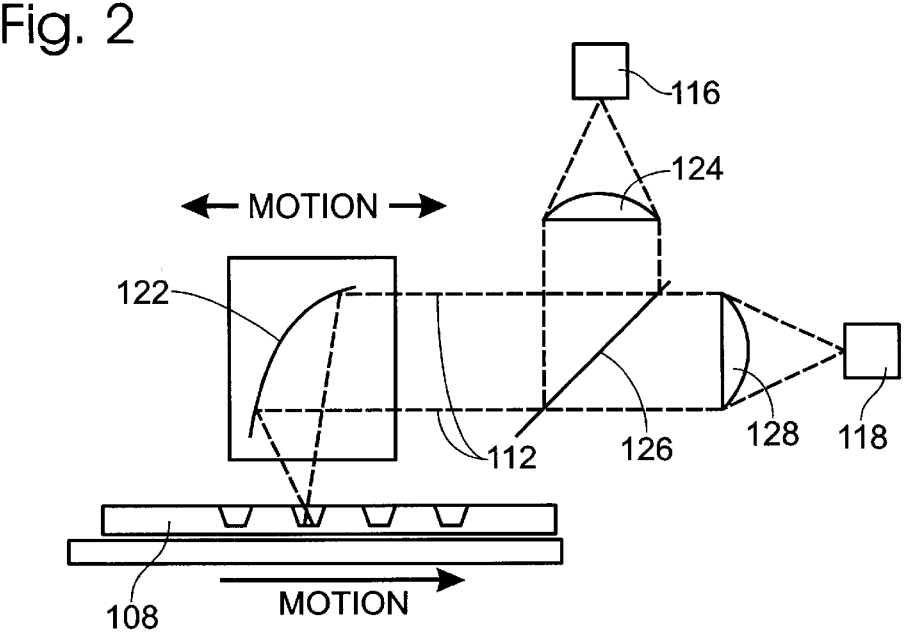
FIG. 2 is an alternative schematic view of the light detection device of FIG. 1.

FIG. 2 is an alternative view of light detection device 100 showing details of the optical relay structures. Here, light 112 is directed from light source 116 (or equivalently from a fiber or other optics operatively connected to light source 116) through a collimating (e.g., convex-plano) lens 124 and onto a beamsplitter 126, which directs a portion of the light toward substrate 108. Light emitted from the substrate is directed onto the beamsplitter, which transmits a portion of the light through a focusing (e.g., a plano-convex) lens 128 toward detector 118 (or equivalently a fiber or other optics operatively connected to detector 118).

Here, reflective element 122 (a parabolic section) may be moved to track the plate motion during integration, and then to "fly-back" quickly to the starting position for the next integration. If the input/output light 112 is collimated, the change in path length will not affect focus, spot size, or light collection, among others. The optics is reflective, which can improve efficiency, optical bandwidth, and cost relative to refractive optics. The moving element can be supported on nonfriction bearings, such as flexures (for example, on a four-bar linkage), because motion is small (~2 mm for a 1536-well plate). Feedback can be provided to reduce positional error of the mirror. In fact, by measuring stage and mirror position and feeding back the error to the mirror drive, the stage and mirror can be locked together so that the mirror tracks the well location substantially exactly, even if the plate motion is not perfectly smooth. This has the significant advantage that substantially precise motion may be accomplished on a much lower mass object (the mirror, instead of the plate and its stage), so that bandwidth is higher and power requirements are lower.

EXAMPLE 2

Figure 3:
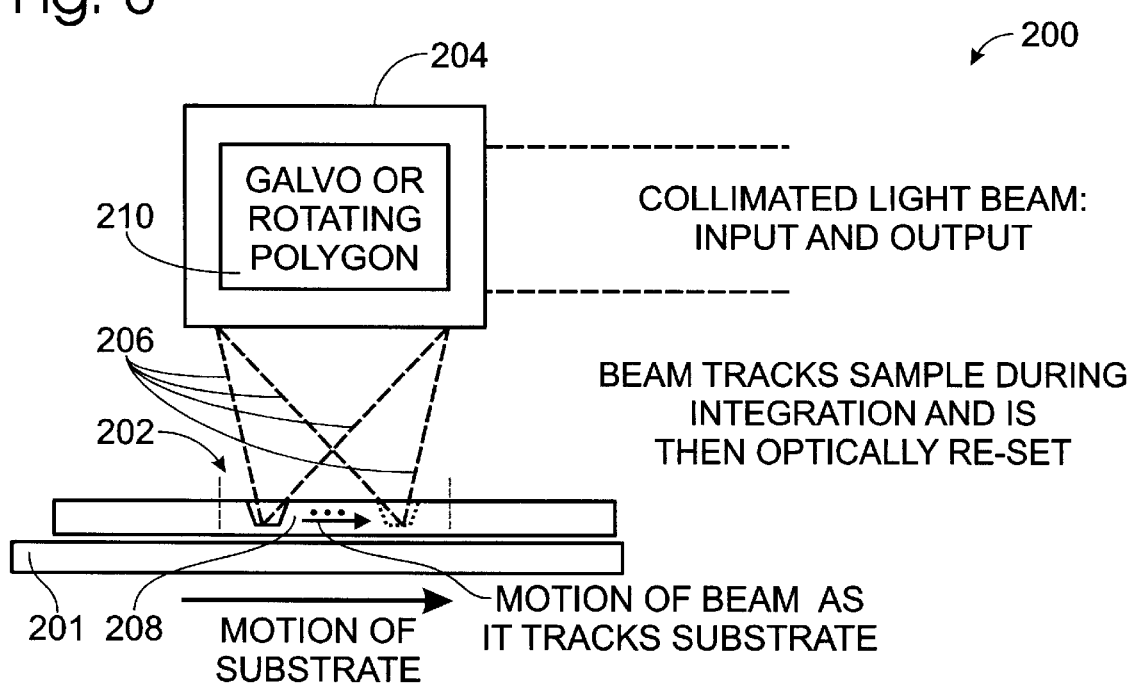
FIG. 3 is a schematic view of an alternative light detection device constructed in accordance with aspects of the invention, showing the device in use to read from a substrate.

FIG. 3 shows an alternative light detection device 200 constructed in accordance with aspects of the invention. Device 200 includes a stage 201, an examination site 202 delimited as above, and an optics head 204 for directing light 206 to and/or from a substrate 208 positioned in the examination site. Device 200 also includes a scanning mechanism 210 configured to scan the substrate. In device 200, the scanning mechanism is configured to move the substrate while holding the optics head fixed. More specifically, the scanning mechanism is configured to rotate rather than translate. Scanning mechanism 212 may include a galvanometer mirror and/or a rotating polygon mirror for matching illumination and/or detection with particular areas of the substrate. Galvanometer mirrors include small planar or convex mirrors attached to the rotating coil of a galvanometer to move a spot of reflected light, among others. Rotating polygon mirrors include a polygonal mirror attached to a driver to move a spot of reflected light, among others.

Device 200 may be used with any light source, although nonlaser light sources, such as arc lamps or LEDs, present special difficulties. This is because the distance between the source and detector may be relatively long, which may result in lower efficiencies with nonlaser light sources. Some of the difficulty may be overcome by using a high color temperature continuous light source, as described in U.S. patent application Ser. No. 09/349,733, which is incorporated herein by reference.

Figure 4:
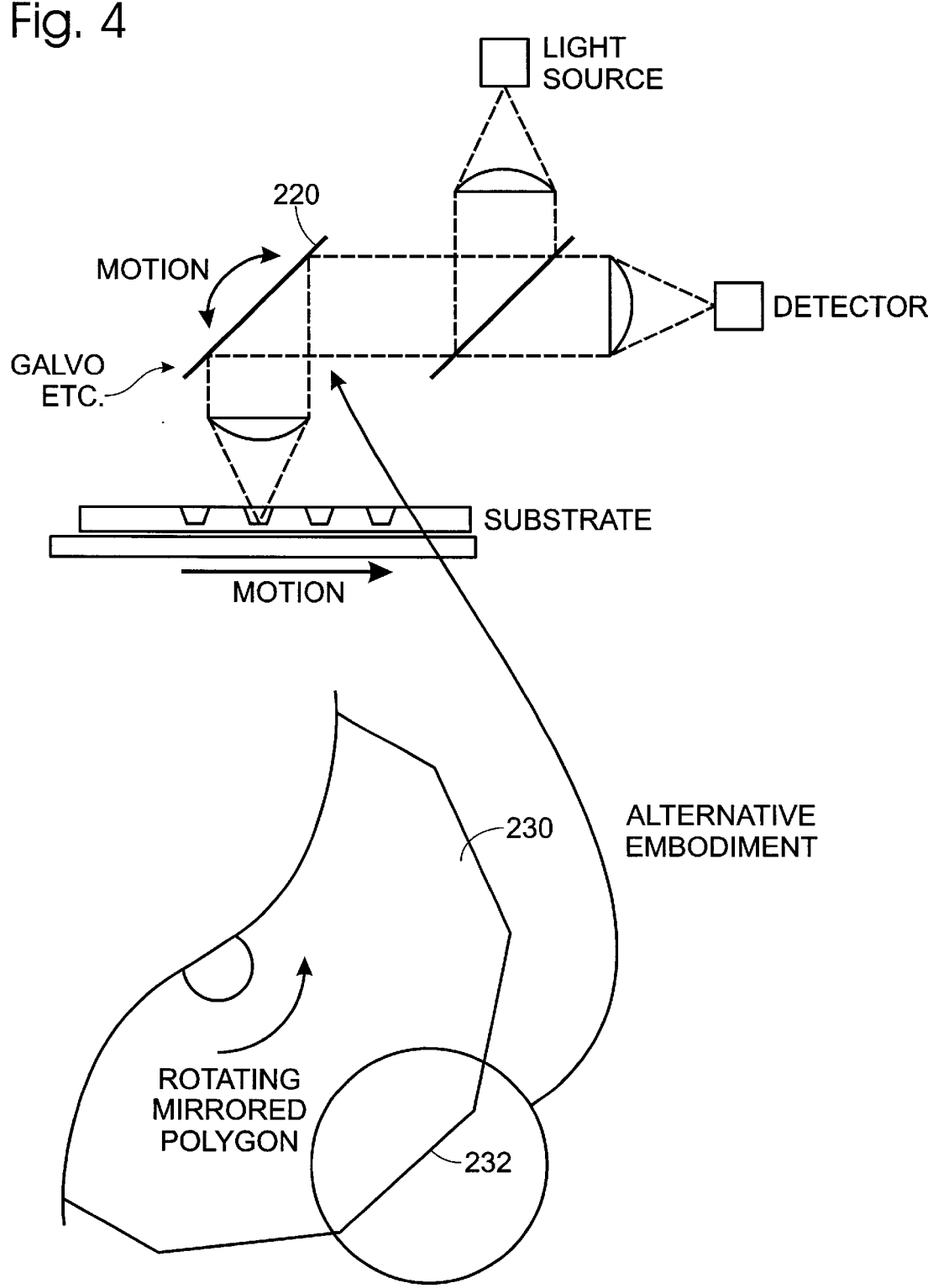
FIG. 4 is an alternative schematic view of the light detection device of FIG. 3.

FIG. 4 shows an alternative view of light detection device 200, illustrating several techniques, including a galvanometer technique and a rotating polygon technique. The optics are substantially as described above for FIG. 2, except that a lens such as a plano-convex, converging, or other positive strength lens is used between the scanning mechanism and the substrate for field flattening.

The primary drawing in FIG. 4 illustrates a galvanometer technique. Here, driven by a galvanometer-type movement, a mirror 220 pivots through a small angle and then returns to its start position to repeat the cycle. Suitable drivers include galvanometers, voice-coil drivers, and piezo drivers. The mirror and driver typically are supported by nonfriction bearings, which may include springs, torsion springs, and/or flexures. A lack of stick-slip enables precise, low-power positioning. The system can be resonant, meaning that the compliance of the bearings resonates with the combined mass of the mirror and driver. If the system is resonant, power requirements will drop significantly. Feedback can be provided as above to reduce positional error of the mirror.

The inset in FIG. 4 illustrates a rotating polygon technique. Here, instead of scanning a mirror back-and-forth as above, a polygonal mirror 230 (or section 232 thereof) rotates in synchrony with the stage. The motor drive may be much easier: if the mirrors are curved, or if an optic is added, the motion may be at constant angular velocity. To reduce dead time between integrations, the polygon should be large compared to the collimated beam. (Dead time occurs when the beam is on two facets of the mirror at once.)

With both the galvanometer and rotating polygon techniques, the focused spot tends to follow an arc. If the plate is planar, resulting difficulties may be corrected by effectively increasing the radius of curvature of the arc by adding a field-flattening optic, by offsetting the axis of rotation of the galvanometer, and/or by providing a rotating polygon with curved faces. Whether corrected or not, the arc will track the sample site in the same direction over the distance scale of the examination region.

EXAMPLE 3

Figure 5A:
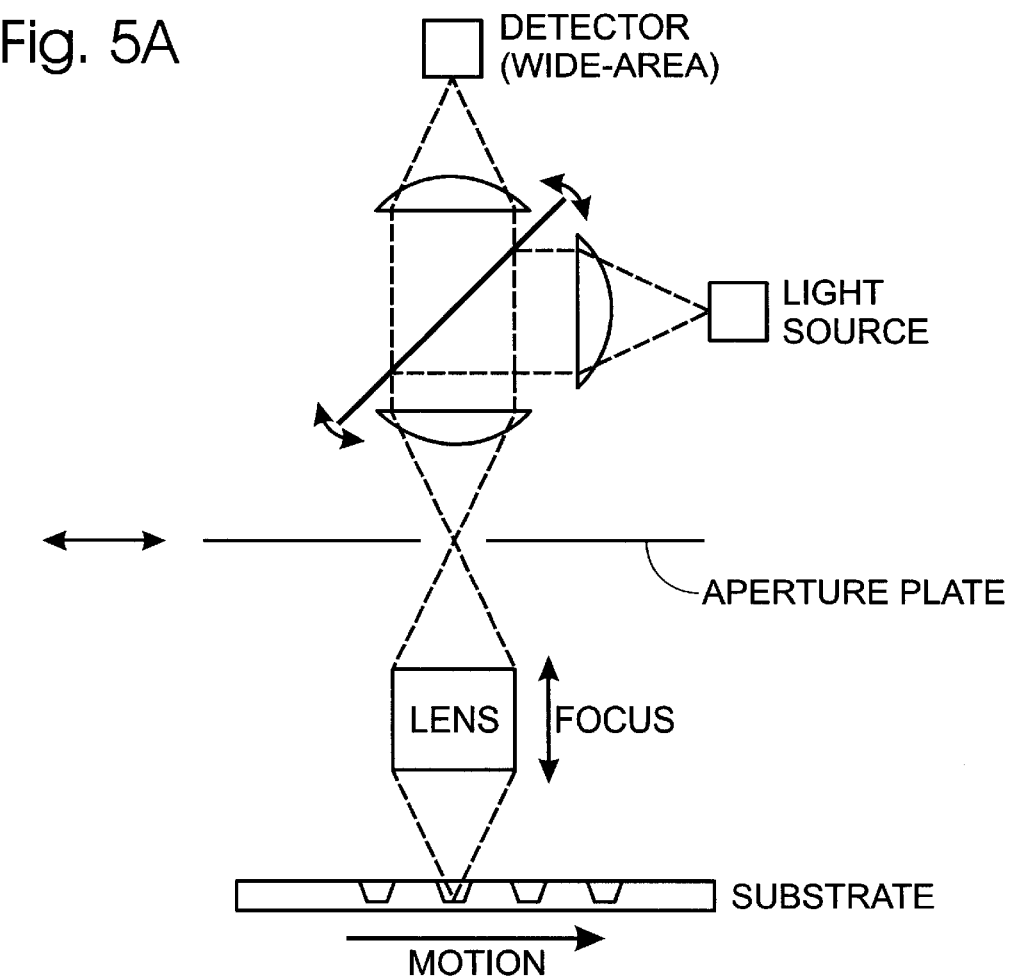
FIGS. 5–7 are schematic views of other alternative light detection devices constructed in accordance with aspects of the invention.
Figure 5B:
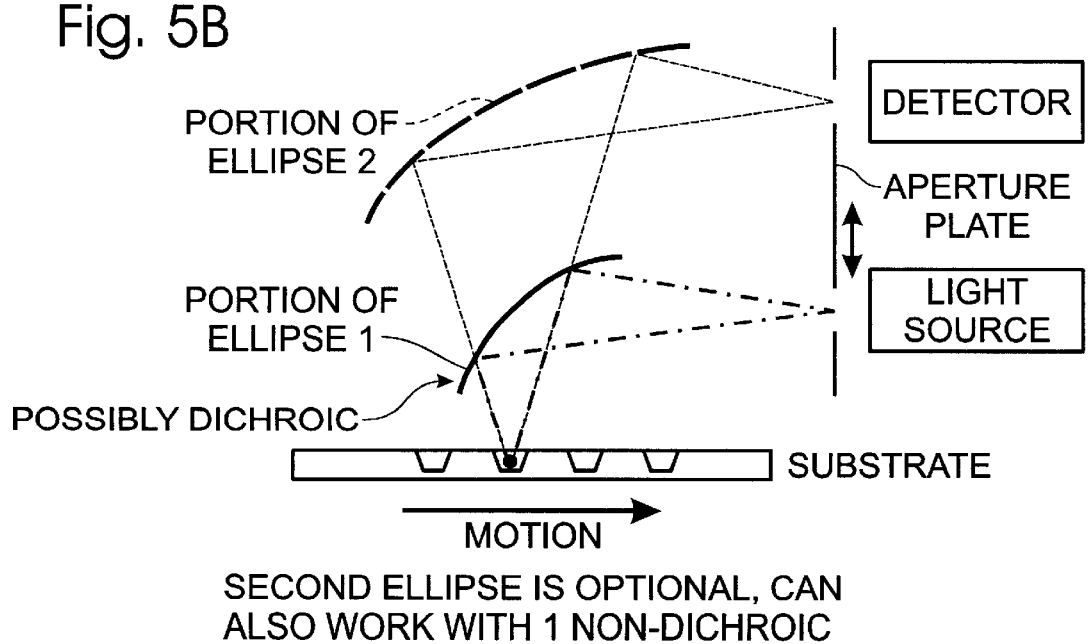
Figure 6A:
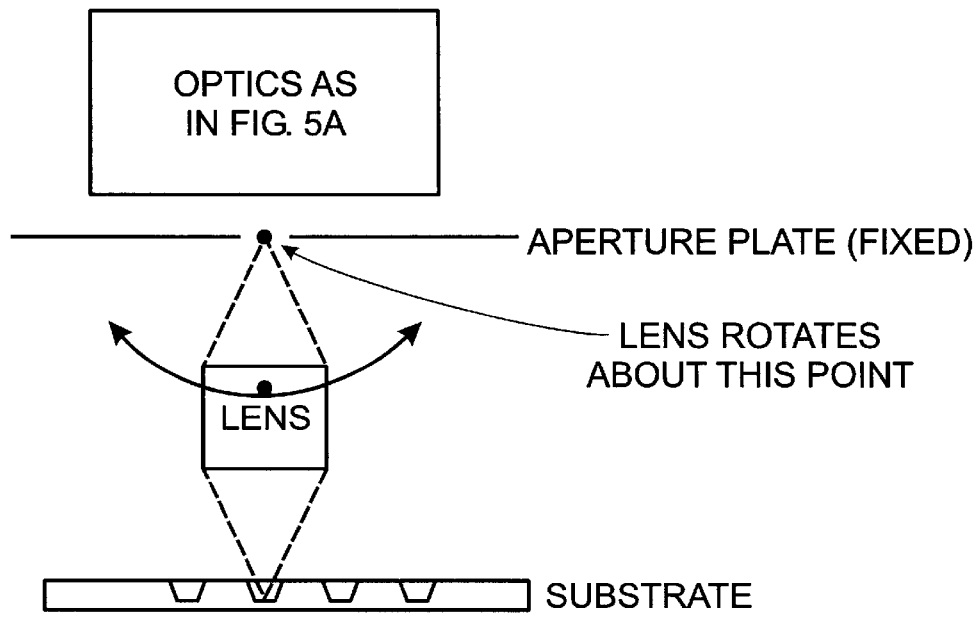
Figure 6B:
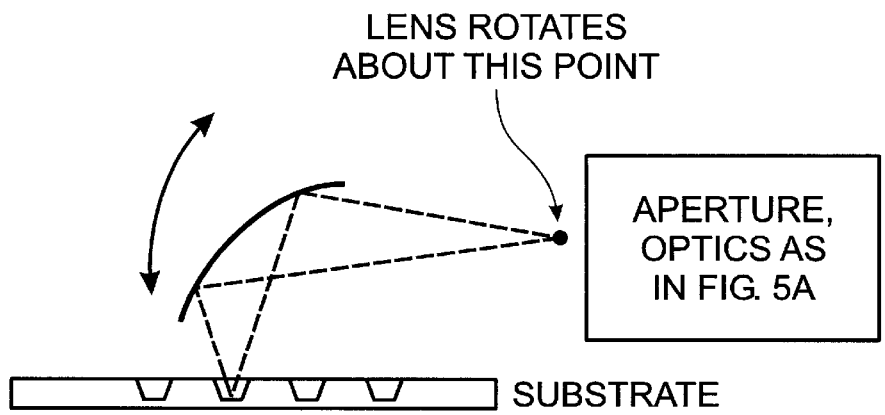

FIGS. 5–6 show other alternative light detection devices constructed in accordance with aspects of the invention. These devices involve scanning an aperture over a larger area detector/source. In these (and other) embodiments, the light may not be collimated as it goes through the scanning mechanism.

FIG. 5 shows a first pair of embodiments involving scanning an aperture. If the detector can accommodate the entire motion of the scanned location (e.g., an area of 2.25 mm×4.5 mm for a 1536-well microplate), which is true with a photomultiplier tube (PMT), and if the source can illuminate it, then only an aperture need be scanned. This is accomplished by imaging a small area of the plate adjacent the well being measured onto a second "aperture plate." The aperture plate is moved in synchrony with the sample plate, but in the opposite direction, so that light to and from only one well can make it through the aperture. If the lens demagnifies by a factor 1/m, then the aperture plate should move at a speed m times the sample plate speed. The subsequent optics has much-relaxed imaging requirements because there is little or no possibility of cross-talk. The aperture plate also could have more than one set of associated optics to increase throughput (requiring multiple imaging elements) or to provide "quick-change" capability for different wavelengths, excitations, etc. The dichroic mirror can pivot to reduce the illuminated area requirement.

A sample plate or other substrate can be imaged onto an "aperture plate" refractively or reflectively, among others. A plate can be imaged refractively using a lens. A plate can be imaged reflectively (with advantages as mentioned above) using a mirror, such as a section of an ellipse. The mirror may be dichroic, which can eliminate all lenses and greatly increase bandwidth; this permits the focus to be adjusted without moving the aperture plate or optics (just the imaging unit), so that the light source(s) and detector(s) can be mounted at the optics head, eliminating the cost and light loss associated with fiber optics. Again, mirrors can be scanned or pivoted to reduce illumination requirements.

FIG. 6 shows a second pair of embodiments involving scanning an aperture. The imaging optics (mirror or lens) can be rotated, or a prism inside the imaging optics can be rotated. Alternatively, the techniques described above can be used with an ellipsoidal mirror, with or without demagnification.

EXAMPLE 4

Figure 7:
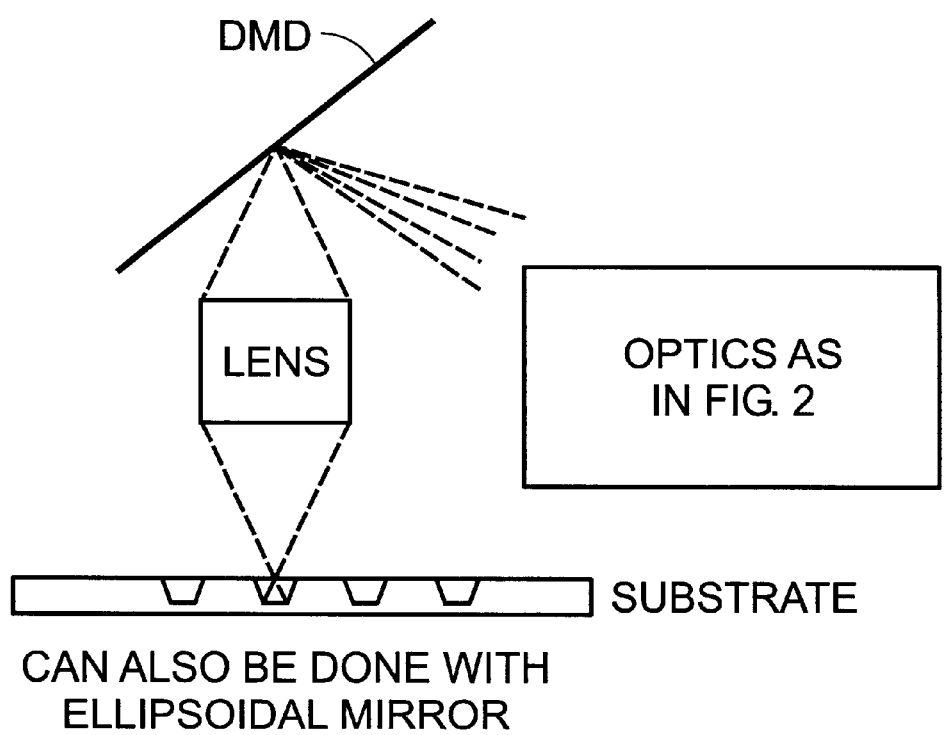

FIG. 7 shows yet another alternative device constructed in accordance with aspects of the invention, using a Digital Mirror Device (DMD). This device has a large array of very small (10–20 micron), very fast mirrors that can be rotated under electronic control. Placed in an image plane, they can be used to control the area that is reflected into the optics. A suitable DMD (used for video projectors) may be obtained commercially from Texas Instruments Inc. (Dallas, Tex.).

EXAMPLE 5

The apparatus and methods for optical detection provided by the invention can be used in a large variety of optical systems and for a large variety of optical applications. This example describes a preferred system, namely a multi-mode high-throughput light-detection system for analyzing samples.

Figure 8:
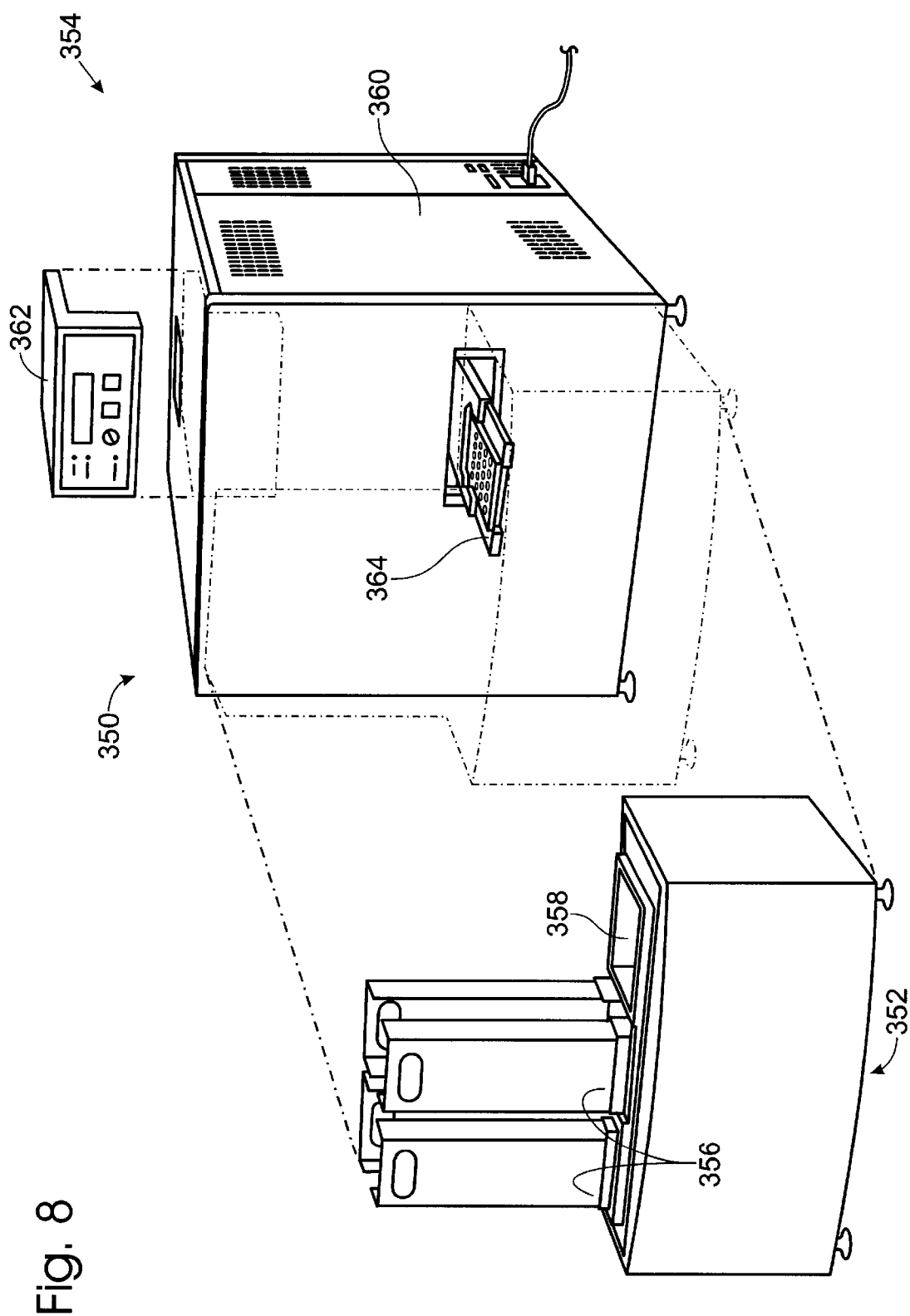
FIG. 8 is a partially exploded perspective view of yet another light detection device constructed in accordance with aspects of the invention, showing a transport module and an analysis module.

FIG. 8 shows such a system 350, which includes a transport module 352 and an analysis module 354 capable of detecting and analyzing light. The transport module includes I/O sites 356, a transfer site 358, and mechanisms (not visible) for transporting sample holders between the I/O and transfer sites, as described above. The analysis module includes a housing 360, a moveable control unit 362, an optical system (not visible), and a transport mechanism 364. The housing may be used to enclose the analysis module, protecting both the user and components of the module, and may be used as a fixed reference point to describe the motions of any moveable portions of the apparatus, such as a scanning optics head. The control unit may be used to operate the module manually and/or robotically, as described in U.S. Pat. No. 6,025,985, which is incorporated herein by reference. The optical system and transport mechanisms are described in subsequent sections.

FIGS. 9–12 show an optical system (and related components) 390 for use in system 350. The optical system may include components for generating and/or detecting light, and for transmitting light to and/or from a sample. These components may include (1) a stage for supporting the sample, (2) one or more light sources for delivering light to the sample, (3) one or more detectors for receiving light transmitted from the sample and converting it to a signal, (4) first and second optical relay structures for relaying light between the light source, sample, and detector, and/or (5) a processor for analyzing the signal from the detector. System components may be chosen to optimize speed, sensitivity, and/or dynamic range for one or more assays. For example, optical components with low intrinsic luminescence may be used to enhance sensitivity in luminescence assays by reducing background. System components also may be shared by different assays, or dedicated to particular assays. For example, steady-state photoluminescence assays may use a continuous light source, time-resolved photoluminescence assays may use a time-varying light source, and chemiluminescence assays may not use a light source. Similarly, steady-state and time-resolved photoluminescence assays may both use a first detector, and chemiluminescence assays may use a second detector.

Optical system 390 includes (a) a photoluminescence optical system, and (b) a chemiluminescence optical system, as described below. Further aspects of the optical system are described in the following patent applications, which are incorporated herein by reference: U.S. patent application Ser. No. 09/160,533, filed Sep. 24, 1998; U.S. patent application Ser. No. 09/349,733, filed Jul. 8, 1999; PCT Patent Application Ser. No. PCT/US99/16287, filed Jul. 26, 1999; and PCT Patent Application Ser. No. PCT/US00/04543, filed Feb. 22, 2000.

a. Photoluminescence Optical System

Figure 9:
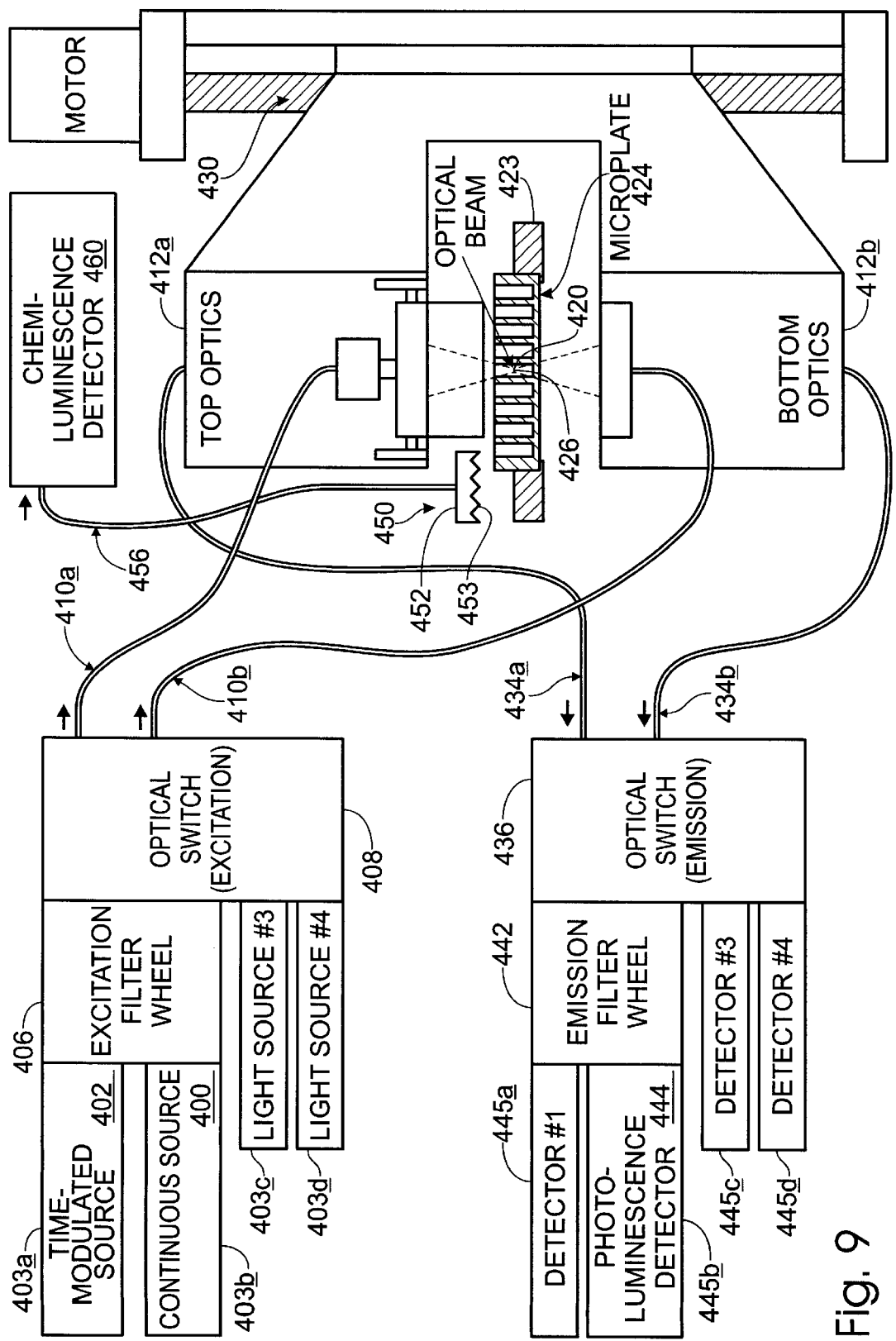
FIG. 9 is a schematic view of an optical system from the analysis module of FIG. 8.
Figure 10:
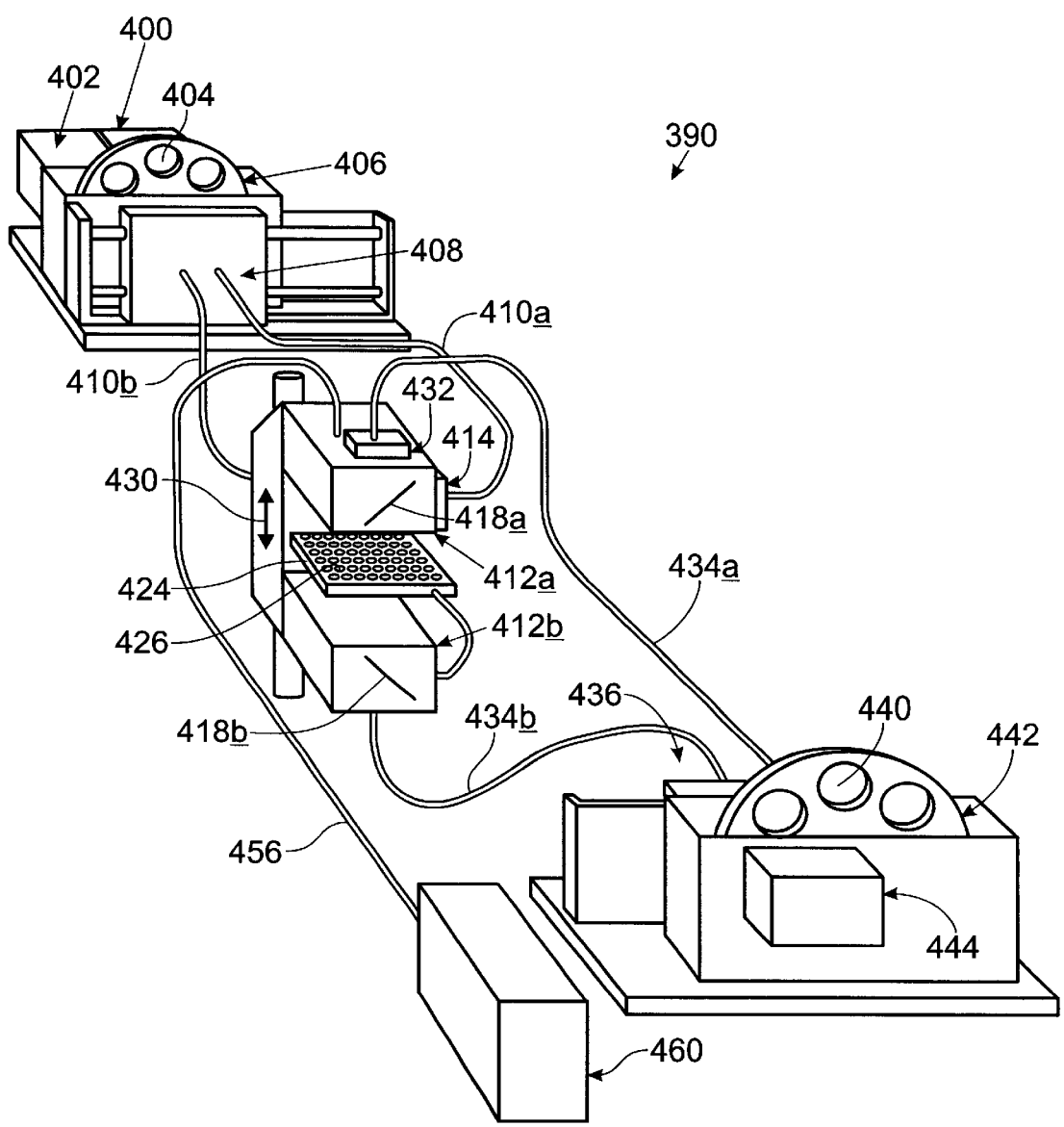
FIG. 10 is a partially schematic perspective view of portions of the apparatus of FIG. 8.
Figure 11:
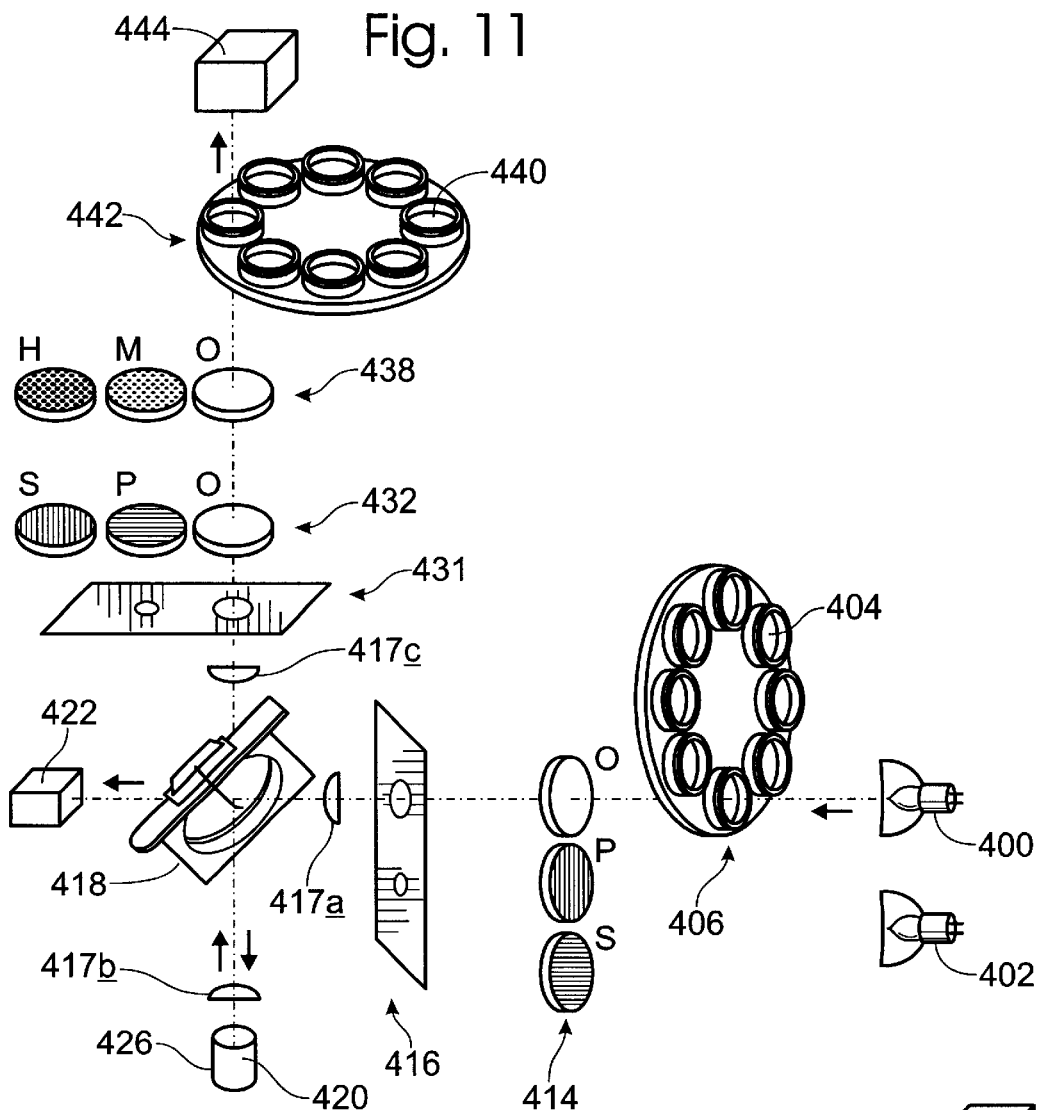
FIG. 11 is a schematic view of photoluminescence optical components from the optical system of FIG. 9.

FIGS. 9–11 show the photoluminescence (or incident light-based) optical system of optical system 390. As configured here, optical system 390 includes a continuous light source 400 and a time-modulated light source 402. Optical system 390 includes light source slots 403a–d for four light sources, although other numbers of light source slots and light sources also could be provided. Light source slots 403a–d function as housings that may surround at least a portion of each light source, providing some protection from radiation and explosion. The direction of light transmission through the incident light-based optical system is indicated by arrows.

Continuous source 400 provides light for absorbance, scattering, photoluminescence intensity, and steady-state photoluminescence polarization assays. Continuous light source 400 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Optical system 390 may include a modulator mechanism configured to vary the intensity of light incident on the sample without varying the intensity of light produced by the light source. Further aspects of the continuous light source are described in U.S. patent application Ser. No. 09/349,733, filed Jul. 8, 1999, which is incorporated herein by reference.

Time-modulated source 402 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockels cell, Kerr cell, or other mechanism. Such other mechanisms may include an amplitude modulator such as a chopper as described in PCT Patent Application Ser. No. PCT/US99/16287, filed Jul. 26, 1999, which is incorporated herein by reference. Extrinsically modulated continuous light sources are especially well suited for frequency-domain measurements.

In optical system 390, continuous source 400 and time-modulated source 402 produce multichromatic, unpolarized, and incoherent light. Continuous source 400 produces substantially continuous illumination, whereas time-modulated source 402 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In optical system 390, spectrum is altered by an excitation interference filter 404, which preferentially transmits light of preselected wavelengths and preferentially absorbs light of other wavelengths. For convenience, excitation interference filters 404 may be housed in an excitation filter wheel 406, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 406 may be mounted in the optical path of some light source slots 403a,b, but not other light source slots 403c,d. Alternatively, the filter wheel may include a blank station that does not affect light passage.

Light next passes through an excitation optical shuttle (or switch) 408, which positions an excitation fiber optic cable 410a,b in front of the appropriate light source to deliver light to top or bottom optics heads 412a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In optical system 390, polarization is altered by excitation polarizers 414, which are included only with top optics head 412a for top reading; however, such polarizers also can be included with bottom optics head 412b for bottom reading. Excitation polarization filters 414 may include an s-polarizer S that passes only s-polarized light, a p-polarizer P that passes only p-polarized light, and a blank O that passes substantially all light, where polarizations are measured relative to the beamsplitter. Excitation polarizers 414 also may include a standard or ferroelectric liquid crystal display (LCD) polarization switching system. Such a system may be faster than a mechanical switcher. Excitation polarizers 414 also may include a continuous mode LCD polarization rotator with synchronous detection to increase the signal-to-noise ratio in polarization assays. Excitation polarizers 414 may be incorporated as an inherent component in some light sources, such as certain lasers, that intrinsically produce polarized light. Further aspects of the polarization filters and their use in polarization assay are described in U.S. patent application Ser. No. 09/349,733, filed Jul. 8, 1999, which is incorporated herein by reference.

Light at one or both optics heads also may pass through an excitation "confocal optics element," which generally comprises any mechanism for focusing light into a "sensed volume." In optical system 390, the confocal optics element includes a set of lenses 417a–c and an excitation aperture 416 placed in an image plane conjugate to the sensed volume, as shown in FIG. 11. Aperture 416 may be implemented directly, as an aperture, or indirectly, as the end of a fiber optic cable. Preferred apertures have diameters of 1 mm and 1.5 mm. Lenses 417a,b project an image of aperture 416 onto the sample, so that only a preselected or sensed volume of the sample is illuminated. The area of illumination will have a diameter corresponding to the diameter of the excitation aperture.

Light traveling through the optics head is directed onto a beamsplitter 418, which reflects light toward a sample 420 and transmits light toward a light monitor 422. The reflected light passes through lens 417b, which is operatively positioned between beamsplitter 418 and sample 420.

Beamsplitter 418 is used to direct excitation or incident light toward the sample and light monitor, and to direct light leaving the sample toward the detector. The beamsplitter is changeable, so that it may be optimized for different assay modes or samples. In some embodiments, switching between beamsplitters may be performed manually, whereas in other embodiments, such switching may be performed automatically. Automatic switching may be performed based on direct operator command, or based on an analysis of the sample by the instrument. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the sample, and while still transmitting considerable light leaving the sample to the detector. If one or a few related photoactive molecules are to be studied, the beamsplitter needs only to be able to accommodate light at a limited number of wavelengths; in this case, a "dichroic" or "multidichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

The beamsplitter more generally comprises any optical device for dividing a beam of light into two or more separate beams. A simple beamsplitter (such as a 50:50 beamsplitter) may include a very thin sheet of glass inserted in the beam at an angle, so that a portion of the beam is transmitted in a first direction and a portion of the beam is reflected in a different second direction. A more sophisticated beamsplitter (such as a dichroic or multi-dichroic beamsplitter) may include other prismatic materials, such as fused silica or quartz, and may be coated with a metallic or dielectric layer having the desired transmission and reflection properties, including dichroic and multi-dichroic transmission and reflection properties. In some beamsplitters, two right-angle prisms are cemented together at their hypotenuse faces, and a suitable coating is included on one of the cemented faces. Further aspects of the beamsplitter are described in PCT Patent Application Ser. No. PCT/US00/06841, filed Mar. 15, 2000, which is incorporated herein by reference.

Light monitor 422 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The sample (or composition) may be held in a substrate (or sample holder) supported by a stage 423. The sample can include compounds, mixtures, surfaces, solutions, emulsions, suspensions, cell cultures, fermentation cultures, cells, tissues, secretions, and/or derivatives and/or extracts thereof. Analysis of the sample may involve measuring the presence, concentration, or physical properties (including interactions) of a photoactive analyte in such a sample. Sample may refer to the contents of a single microplate well, or several microplate wells, depending on the assay.

The system and its components may be used with a variety of substrates. As used here, "substrate" generally comprises any material, surface, or other holder capable of supporting a sample for use in optical spectroscopy, and preferably for use with automated sample handling equipment. The substrate may support discrete or continuous samples, where sample sites refer to the locations of discrete samples or the locations of different regions within a continuous sample, respectively. The substrate may support samples at low, intermediate, or high density, and be designed for single or multiple use.

Representative sample holders include microplates, PCR plates, biochips, and chromatography plates, among others. A microplate is a multi-well sample holder, typically but not exclusively used for luminescence applications. A PCR plate is a multi-well sample holder used for performing PCR. Preferred PCR plates would include a footprint, well spacing, and well shape similar to those of the preferred microplates, while possessing a stiffness adequate for automated handling and a thermal stability adequate for PCR. A biochip is a small, flat surface (such as a glass or silicon wafer, a semiconductor chip, or a multiple-well CCD) onto which biomolecules (such as nucleic acids and proteins) are immobilized in distinct spots or arrays. Biochips include DNA chips, DNA microarrays, gene arrays, and gene chips, among others. Preferred biochips are described in Bob Sinclair, *Everything's Great When It Sits on a Chip: A Bright Future for DNA Arrays,* 13 The Scientist, May 24, 1999, at 18. As defined here, a chromatography plate is a flat surface used for performing chromatography, electrophoresis, or other separations.

In optical system 390, the preferred sample holder is a microplate 424, which includes a plurality of discrete microplate wells 426 for holding samples. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in an 8×12 rectangular array on 9-millimeter centers. Preferred microplates are described in U.S. patent application Ser. No. 09/478,819, filed Jan. 5, 2000, which is incorporated herein by reference.

The sensed volume generally comprises any volume from which light is detected, and preferably any volume from which light is substantially exclusively detected. The sensed volume may have an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in U.S. patent application Ser. No. 09/478,819, filed Jan. 5, 2000, which is incorporated herein by reference.

The position of the sensed volume can be moved precisely within the sample to optimize the signal-to-noise and signal-to-background ratios. For example, the sensed volume may be moved away from walls or other boundary interfaces in the sample holder to optimize signal-to-noise and signal-to-background ratios, reducing spurious signals that might arise from luminophores bound to the walls and thereby immobilized. In optical system 390, position in the X,Y-plane perpendicular to the optical path is controlled by moving the stage supporting the sample, whereas position along the Z-axis parallel to the optical path is controlled by moving the optics heads using a Z-axis adjustment mechanism 430, as shown in FIGS. 9 and 10. However, any mechanism for bringing the sensed volume into alignment or register with the appropriate portion of the sample also may be employed. In particular, mechanisms such as those presented above in Examples 1–4 may be employed for bringing the sensed volume into alignment with a preselected portion of a moving sample holder and for maintaining that alignment during sample reading.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In optical system 390, epi modes are supported, so the excitation and emission light travel the same path in the optics head, albeit in opposite or anti-parallel directions. However, trans modes also can be used with additional sensors, as described below. In optical system 390, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light may be transmitted by the sample in multiple directions. A portion of the transmitted light will follow an emission pathway to a detector. Transmitted light passes through lens 417c and may pass through an emission aperture 431 and/or an emission polarizer 432. In optical system 390, the emission aperture is placed in an image plane conjugate to the sensed volume and transmits light substantially exclusively from this sensed volume. In optical system 390, the emission apertures in the top and bottom optical systems are the same size as the associated excitation apertures, although other sizes also may be used. The emission polarizers are included only with top optics head 412a. The emission aperture and emission polarizer are substantially similar to their excitation counterparts. Emission polarizer 432 may be included in detectors that intrinsically detect the polarization of light.

Excitation polarizers 414 and emission polarizers 432 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 418 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 434a,b to an emission optical shuttle (or switch) 436. This shuttle positions the appropriate emission fiber optic cable in front of the appropriate detector. In optical system 390, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In optical system 390, intensity is altered by emission neutral density filters 438, which absorb light substantially independent of its wavelength, dissipating the absorbed energy as heat. Emission neutral density filters 438 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and diffractive beam splitters (e.g., acousto-optic modulators), which deflect light along different paths through diffraction. Examples also include hot mirrors or windows that transmit light of some wavelengths and absorb light of other wavelengths.

Light next may pass through an emission interference filter 440, which may be housed in an emission filter wheel 442. In optical system 390, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the sample, among other factors.

Light last passes to a detector, which is used in absorbance, scattering and photoluminescence assays, among others. In optical system 390, there is one detector 444, which detects light from all modes. A preferred detector is a photomultiplier tube (PMT). Optical system 390 includes detector slots 4145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT Patent Application Ser. No. PCT/US99/03678.

b. Chemiluminescence Optical System

Figure 12:
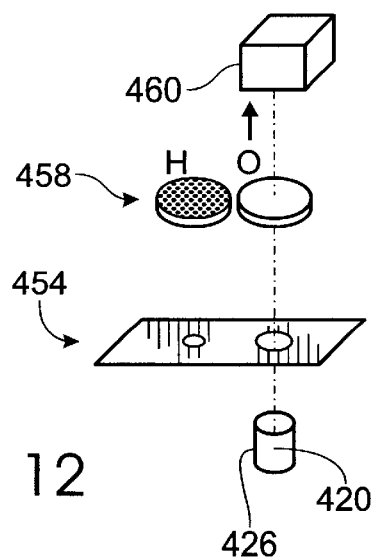
FIG. 12 is a schematic view of chemiluminescence optical components from the optical system of FIG. 9.

FIGS. 9, 10, and 12 show the chemiluminescence optical system of optical system 390. Because chemiluminescence follows a chemical event rather than the absorption of light, the chemiluminescence optical system does not require a light source or other excitation optical components. Instead, the chemiluminescence optical system requires only selected emission optical components. In optical system 390, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent sample 420 held in a sample holder 426. The sample and sample holder are analogous to those used in photoluminescence assays; however, analysis of the sample involves measuring the intensity of light generated by a chemiluminescence reaction within the sample rather than by light-induced photoluminescence. A familiar example of chemiluminescence is the glow of the firefly.

Chemiluminescence light typically is transmitted from the sample in all directions, although most will be absorbed or reflected by the walls of the sample holder. A portion of the light transmitted through the top of the well is collected using a chemiluminescence head 450, as shown in FIG. 9, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the sample. Detecting from a sensed volume reduces contributions to the chemiluminescence signal resulting from "cross talk," which is pickup from neighboring wells. The nonconfocal mechanism includes a chemiluminescence baffle 452, which includes rugosities 453 that absorb or reflect light from other wells. The nonconfocal mechanism also includes a chemiluminescence aperture 454 that further confines detection to a sensed volume.

Light next passes through a chemiluminescence fiber optic cable 456, which may be replaced by any suitable mechanism for directing light from the sample toward the detector. Fiber optic cable 456 is analogous to excitation and emission fiber optic cables 410*a,b* and 434*a,b* in the photoluminescence optical system. Fiber optic cable 456 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In optical system 390, intensity is altered by chemiluminescence neutral density filters 458. Light also may pass through other filters, if desired.

Light last passes to a detector, which converts light into signals that may be processed by the apparatus. In optical system 390, there is one chemiluminescence detector 460. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

Although the invention has been disclosed in its preferred forms, the specific embodiments thereof as disclosed and illustrated herein are not to be considered in a limiting sense, because numerous variations are possible. For example, the apparatus and methods described herein may be used with any of the light detection devices, light detection methods, and/or sample holders described in the above-identified patent applications. The invention may be used for fluorescence and phosphorescence measurements, which involve illuminating with light of one wavelength and detecting light of a longer wavelength. The invention also may be used for epi-absorption measurements, which involve illuminating with and detecting light of the same wavelength. The invention also may be used for chemiluminescence measurements, which involve only detecting light. Applicants regard the subject matter of their invention to include all novel and nonobvious combinations and subcombinations of the various elements, features, functions, and/or properties disclosed herein. No single feature, function, element, or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. An apparatus for detecting light transmitted from a substrate having a plurality of sample sites, the apparatus comprising:

a stage for supporting the substrate, the stage being configured to move the substrate in a first direction so that the sample sites pass sequentially through an examination region delimited by a detection initiation position and a detection termination position;

a detector configured to detect light;

an optical relay structure configured to transmit light from a sensed volume within the examination region to the detector, the sensed volume being smaller than the examination region; and an automated scanning mechanism configured to move the sensed volume in the first direction between the detection initiation position and the detection termination position;

wherein the sensed volume tracks a first sample site as it moves between the initiation position and the termination position, so that light transmitted by the first sample can be detected by the detector.

2. The apparatus of claim 1, wherein the sensed volume returns to the initiation position after the first sample site passes the termination position to track the next sample site as it moves between the initiation position and the termination position.

3. The apparatus of claim 1 further comprising a light source, where the optical relay structure further is configured to transmit light from the light source to the sensed volume.

4. The apparatus of claim 1, wherein the sample sites move at a substantially constant speed through the examination region.

5. The apparatus of claim 1, wherein the time required for the sensed volume to return to the initiation position is less than the time required for the sensed volume to track a sample site as it moves between the initiation position and the termination position.

6. The apparatus of claim 1, wherein the scanning mechanism includes reflective optics.

7. The apparatus of claim 6, wherein the reflective optics is selected from the group consisting of a parabolic mirror, a polygonal mirror, and a galvanometer mirror.

8. The apparatus of claim 6, wherein at least a portion of the reflective optics undergoes translational motion to track the sample sites.

9. The apparatus of claim 6, wherein at least a portion of the reflective optics undergoes rotational motion to track the sample sites.

10. The apparatus of claim 1, wherein the scanning mechanism includes refractive optics.

11. The apparatus of claim 6, wherein the detector includes a wide area detection device, and the scanning mechanism includes a light blocking member having an aperture positioned between the detection device and the examination region so that sensed volume tracking through the examination region is facilitated by moving the light blocking member relative to the wide area detection device.

12. The apparatus of claim 1, wherein the substrate is selected from the group consisting of a microplate, a biochip, and a chromatography plate.

13. The apparatus of claim 12, wherein the substrate is a microplate and the sample sites are wells in the microplate.

14. The apparatus of claim 1, wherein the separation between the first and second sample sites exceeds the separation between the initiation position and the termination position.

15. The apparatus of claim 1 further comprising a housing configured to support and enclose a least a portion of the apparatus, where the initiation position and the termination position are referenced relative to a fixed portion of the housing.

16. The apparatus of claim 1, wherein the first sample site moves past the termination position before the second sample site moves into the initiation position.

17. The apparatus of claim 1, wherein the light transmitted from the substrate includes light selected from the group consisting of fluorescence, phosphorescence, and chemiluminescence.

18. The apparatus of claim 1, the composition being contained in a spatial volume lying between boundary interfaces located at different points along a Z-axis, wherein the Z-axis is substantially perpendicular to the stage.

19. The apparatus of claim 1, wherein the substrate further includes a third sample site, and wherein the sensed volume returns to the initiation position after the second sample site passes the termination position to track the third sample site as it moves between the initiation position and the termination position.

20. An apparatus for detecting light transmitted from a sample site, the apparatus comprising:

a stage for supporting a substrate containing the sample site;

a detector configured to detect light;

an optical relay structure positioned between the stage and the detector and configured to transmit light from a sensed volume to the detector; and a support structure configured to support the stage, the detector, and the optical relay structure;

where the stage and the optical relay structure are configured to align the sample site and the sensed volume automatically and to maintain that alignment while moving the sample site relative to a fixed portion of the support structure, so that light transmitted from the sample site can be detected by the detector as the sample site is moved.

21. The apparatus of claim 20, wherein the optical relay structure includes an automated scanning mechanism that moves the sensed volume with the sample site relative to the fixed portion of the support structure.

22. The apparatus of claim 20, wherein the scanning mechanism includes reflective optics.

23. The apparatus of claim 22, wherein the reflective optics is selected from the group consisting of a parabolic mirror, a polygonal mirror, and a galvanometer mirror.

24. The apparatus of claim 22, wherein at least a portion of the reflective optics undergoes translational motion to track the sample sites.

25. The apparatus of claim 22, wherein at least a portion of the reflective optics undergoes rotational motion to track the sample sites.

26. The apparatus of claim 20, wherein the scanning mechanism includes refractive optics.

27. The apparatus of claim 22, wherein the detector includes a wide area detection device, and the scanning mechanism includes a light blocking member having an aperture positioned between the detection device and the examination region so that sensed volume tracking through the examination region is facilitated by moving the light blocking member relative to the wide area detection device.

28. The apparatus of claim 20, the sample site being a first sample site, where the substrate contains a plurality of sample sites, and where the stage and the optical relay structure are configured to align the sample sites serially with the sensed volume.

29. An apparatus for detecting light transmitted from a sample, the apparatus comprising:

a support structure having a stage for supporting a substrate containing the sample; and means for detecting light from a sensed volume in the sample while the sensed volume and the sample move substantially together relative to the support structure.

30. A method of detecting light transmitted from a substrate having first and second sample sites, the method comprising:

moving the substrate in a first direction so that the first and second sample sites pass sequentially through an initiation position and a termination position;

aligning a sensed volume with the first sample site at the initiation position and maintaining the alignment while detecting light transmitted from the sensed volume as the first sample site moves from the initiation position to the termination position; and aligning the sensed volume with the second sample site at the initiation position and maintaining the alignment while detecting light transmitted from the sensed volume as the second sample site moves from the initiation position to the termination position.

31. The method of claim 30, wherein each maintaining step includes the step of moving a reflective optics member.

32. The method of claim 31, wherein the reflective optics member is selected from the group consisting of a parabolic mirror, a polygonal mirror, and a galvanometer mirror.

33. The method of claim 30, wherein each maintaining step includes the step of rotating the reflective optics member.

34. The method of claim 30, wherein each maintaining step includes the step of moving a refractive optics member.

* * * * *